United States Patent

Goh et al.

[11] Patent Number: 5,258,039
[45] Date of Patent: Nov. 2, 1993

[54] ENERGY STORING COMPOSITE PROSTHETIC FOOT

[75] Inventors: James C. H. Goh; S. L. Toh; T. E. Tay, all of Singapore, Singapore

[73] Assignee: The National University of Singapore, Singapore

[21] Appl. No.: 793,082

[22] Filed: Nov. 15, 1991

[51] Int. Cl.⁵ .............................................. A61F 2/66
[52] U.S. Cl. ........................................ 623/55; 623/52
[58] Field of Search ................................... 623/47-56

[56] References Cited

U.S. PATENT DOCUMENTS

| | | | |
|---|---|---|---|
| 65,185 | 5/1867 | Emery | 623/54 X |
| 2,440,075 | 4/1948 | Campbell | 623/50 |
| 2,453,969 | 11/1948 | Carter | 623/52 |
| 2,556,525 | 6/1951 | Drennon | 623/49 |
| 4,547,913 | 10/1985 | Phillips | 623/27 |
| 4,645,509 | 2/1987 | Poggi et al. | 623/55 |
| 4,721,510 | 1/1988 | Cooper et al. | 623/53 X |
| 4,822,363 | 4/1989 | Phillips | 623/27 |
| 5,037,444 | 8/1991 | Phillips | 623/55 |
| 5,062,859 | 11/1991 | Naeder | 623/55 |

FOREIGN PATENT DOCUMENTS

| | | | |
|---|---|---|---|
| 0405686 | 11/1924 | Fed. Rep. of Germany | 623/53 |
| 2640499 | 6/1990 | France | 623/53 |
| 0778732 | 12/1980 | U.S.S.R. | 623/55 |
| 8909036 | 10/1989 | World Int. Prop. O. | 623/53 |

Primary Examiner—Randall L. Green
Assistant Examiner—D. Willse
Attorney, Agent, or Firm—Lowe, Price, LeBlanc & Becker

[57] ABSTRACT

An energy storing composite prosthetic foot (and its modification) which allows an amputee to walk and run smoothly with less effort than when using a traditional prosthetic foot is disclosed. It is fabricated from a resin impregnated, high strength carbon woven fabric which offers high energy return characteristics to give the wearer high mobility with a more natural feel. The invention also incorporates a mechanism to provide flexibility in inversion/eversion, a feature which traditional feet fail to achieve.

4 Claims, 10 Drawing Sheets

ENERGY STORING COMPOSITE PROSTHETIC FOOT

BACKGROUND OF THE INVENTION

1. Field of the Invention

The present invention relates to prosthetic devices and, more particularly to prosthetic foot.

2. Prior Art

Traditional prosthetic feet are usually manufactured from materials which are relatively rigid and are of relatively high weight. As a result, the wearer of prior art prosthetic feet are restricted to slow and non-strenuous activities.

In addition, the wearer is unable to push off after the foot is flat which becomes more evident when the speed of motion is increased.

Relevent to the present invention are the teachings of U.S. Pat. Nos. 4,547,913 and 4,822,363 which disclosed prostheses having a foot portion as well as a leg portion. However, the present invention does not include a leg portion which allows the foot to be attached to more conventional pylons.

Moreover, traditional prosthetic foot has no flexibility in inversion/eversion which makes walking on uneven ground uncomfortable. The present invention includes a design which improves flexibility in inversion/eversion.

BRIEF SUMMARY OF THE INVENTION

A prosthetic foot which allows an amputee to walk and run smoothly with less effort than when using a traditional prosthetic foot is disclosed. The prosthetic foot utilises a resin impregnated carbon woven fabric composite material. The carbon woven fabric composits material is characterised by its high strength-to-weight ratio, durability, good fatigue properties and corrosion resistance. More importantly, structures made from this composite material are capable of resulting in high energy return characteristics. The energy stored during heel strike is later used during push-off. This gives the wearer a high mobility with a more natural feel.

A design to increase flexibility in inversion/eversion of the foot is also disclosed. It enables the wearer to walk comfortably on uneven ground.

A total of six designs are disclosed.

BRIEF DESCRIPTION OF THE DRAWINGS

The invention will now be described with reference to the drawings in which.

DETAILED DESCRIPTION OF THE INVENTION

Figure 1:
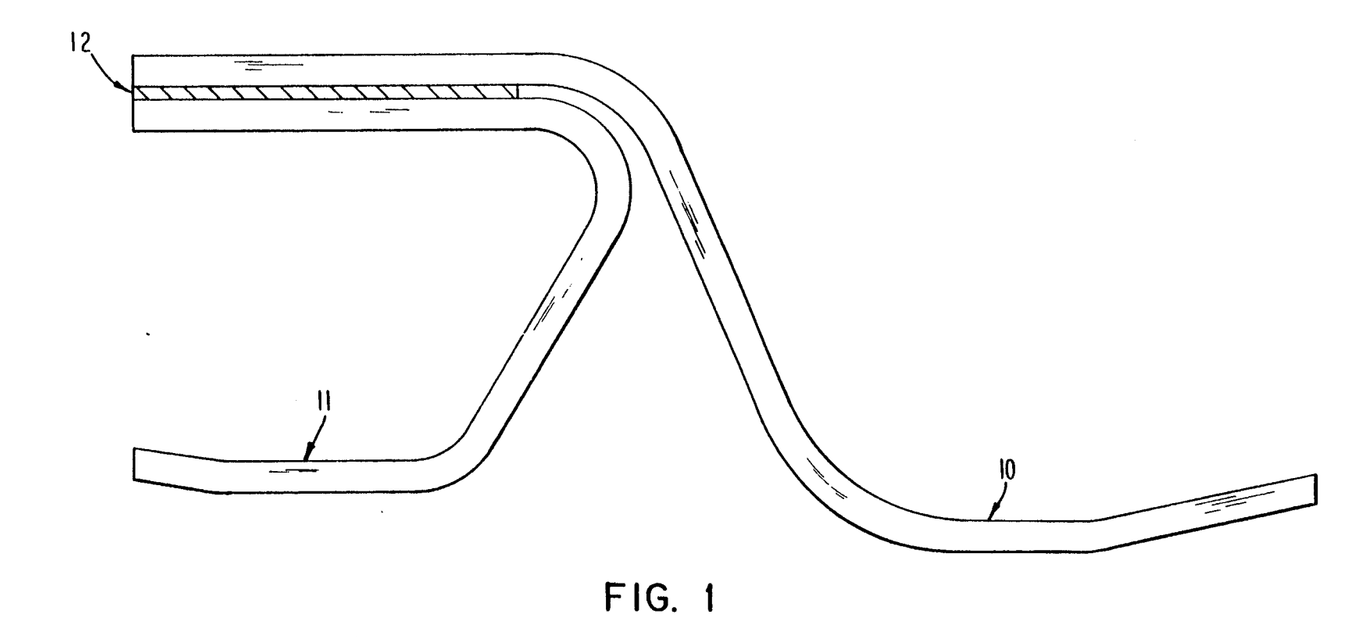
FIG. 1 is a side view of one invention.
Figure 2:
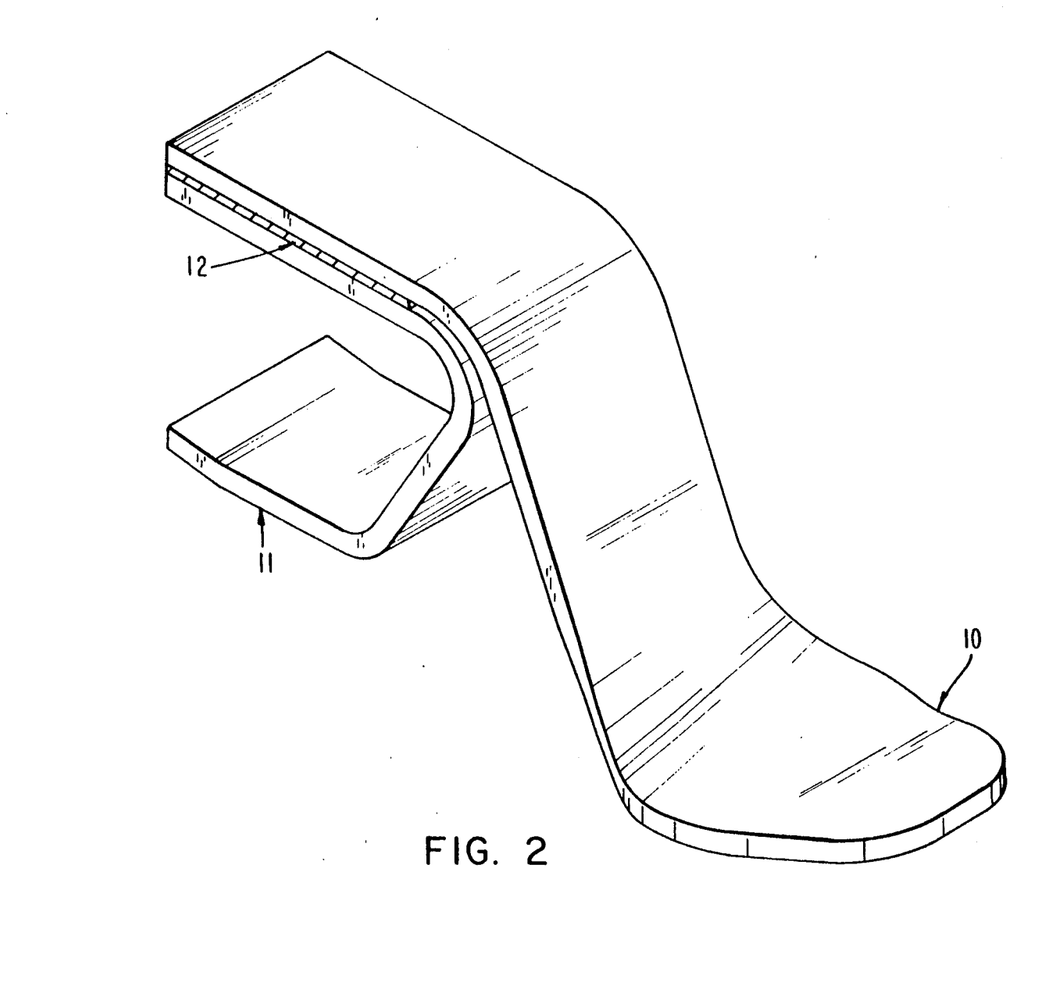
FIG. 2 is a 3-D view of the device of FIG. 1.

First referring to FIG. 1 and FIG. 2, there are shown a side view and 3-D view of one of the designs. The forefoot portion 10 extends horizontally from the ankle region anteriorly toward the toe region at the front of the foot whereas the heel portion 11 extends horizontally forward from the horizontal ankle region and curves downward and extends to the posterior of the foot. Both the forefoot portion 10 and heel portion 11 are designed to serve as flat spring-like leaves so that the foot provides a strong cushioning and energy storage effect.

Figure 4:
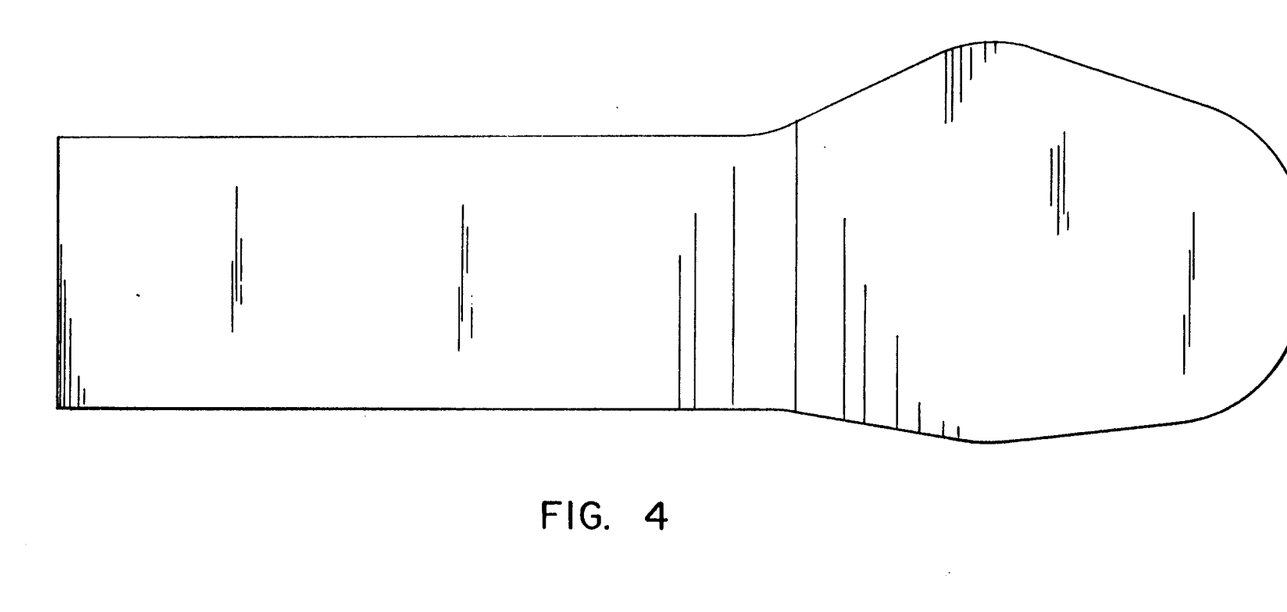
FIG. 4 is a plan view of the device of FIG. 1.

Now referring to FIG. 4, which is a plan view of the design, it is observed that the forwardly extending forefoot portion is contoured to resemble the shape of an insole. This makes the foot more accommodating when worn together with a rubber foam in a shoe and gives the foot stability.

Figure 3:
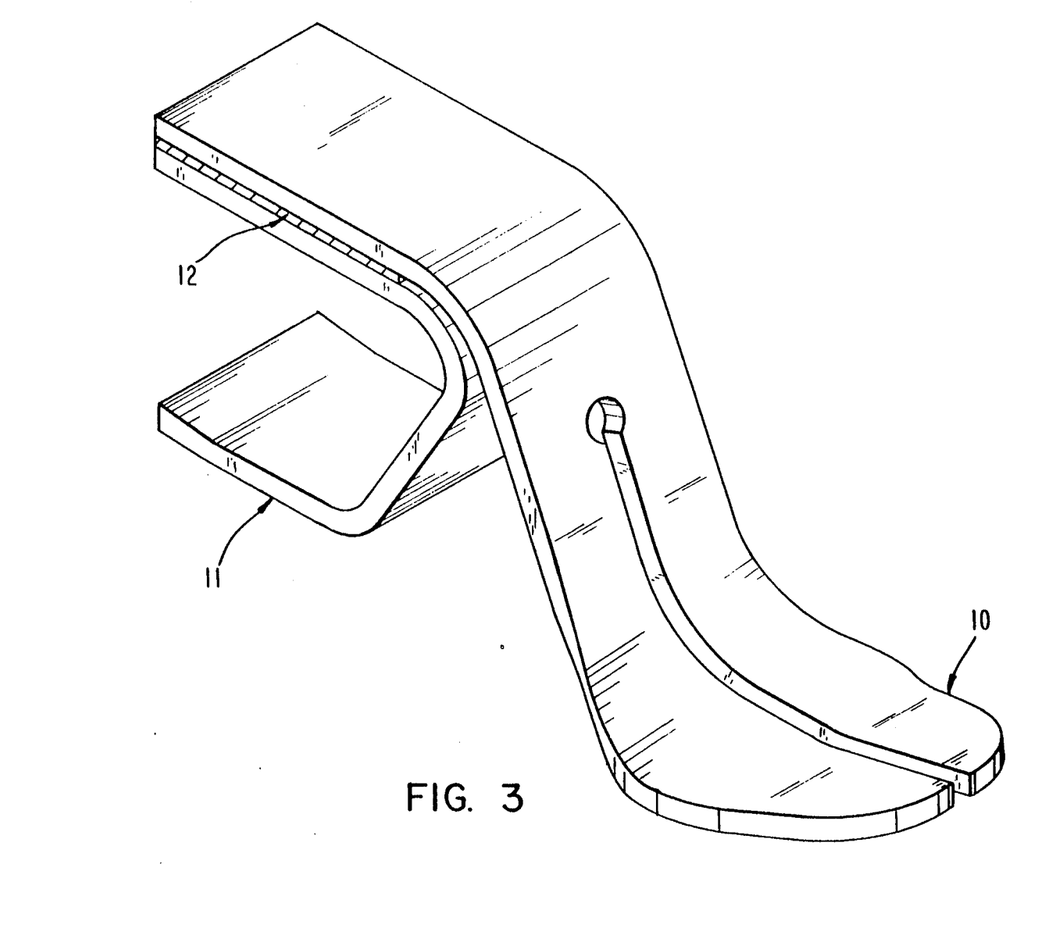
FIG. 3 is a 3-D view of the device of FIG. 1 modified with a slit to provide for inversion/eversion.

In the design shown in FIG. 1 to FIG. 3, an elastomeric ankle pad 12 is added between the forefoot portion 10 and heel portion 11 at the ankle region to increase the compliance of the foot.

The prosthetic foot is fabricated using a resin impregnated carbon fibre woven fabric. The laminate consists of a combination of on-axis and off-axis laminae to provide strength in various directions. Although prototypes using the above-mentioned material gave excellent results during testing, prototypes made of other material like KEVLAR carbon woven fabric proved to be equally competent, if not better.

Deflection tests conducted according to the VAPC standards showed that the forefoot portion 10 and heel portion 11 are slightly stiff. Excellent results were obtained when the prototypes were made thinner.

Now referring to FIG. 3, an additional feature of the present invention is a slit which extends from the toe region to approximately midway of the forefoot portion 10, ending with a hole wider than the slit to reduce stress concentration at the end of the slit. This feature offers flexibility in inversion/eversion and makes the foot to be more accommodating when the wearer walks on uneven ground. Prior prosthetic feet generally have no flexibility in inversion/eversion.

Figure 5:
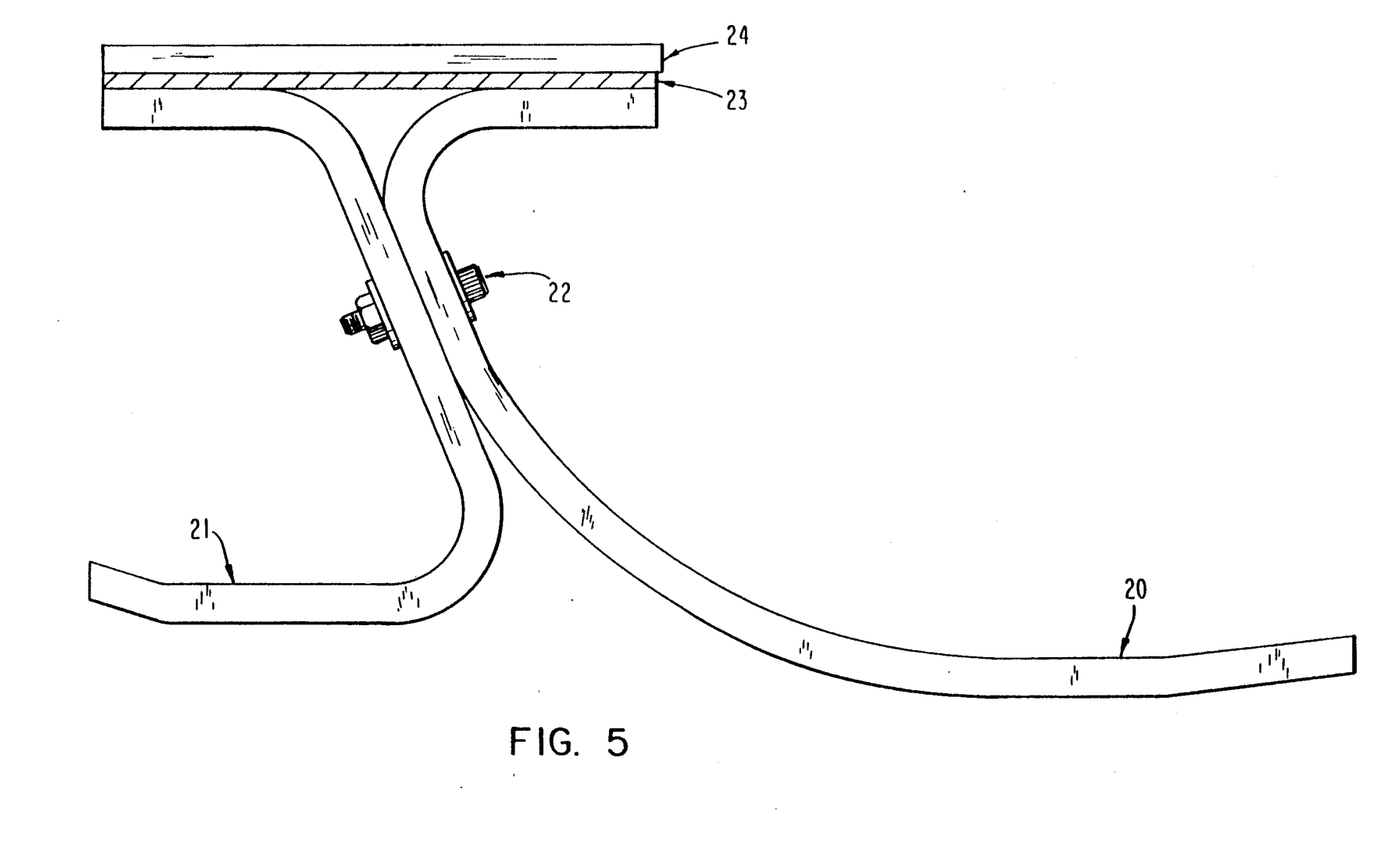
FIG. 5 is a side view of one invention.
Figure 6:
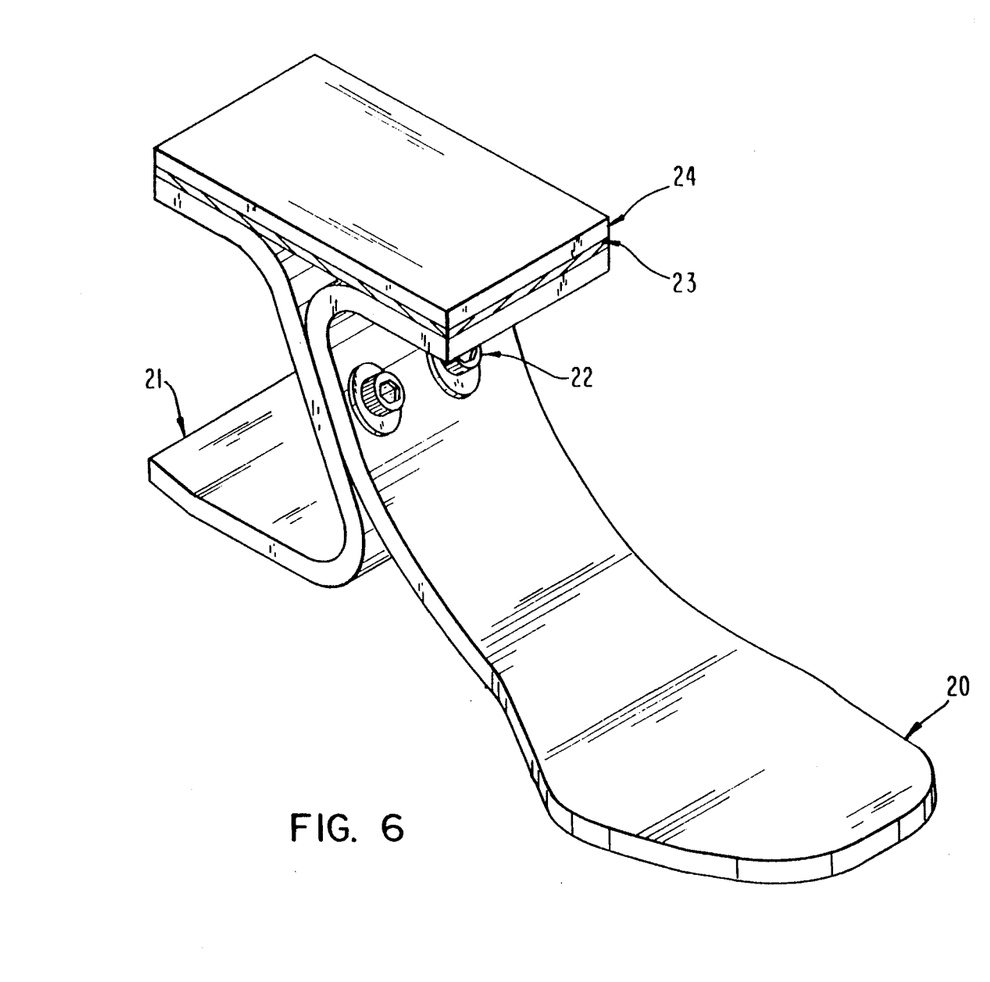
FIG. 6 is a 3-D view of the device of FIG. 5.
Figure 7:
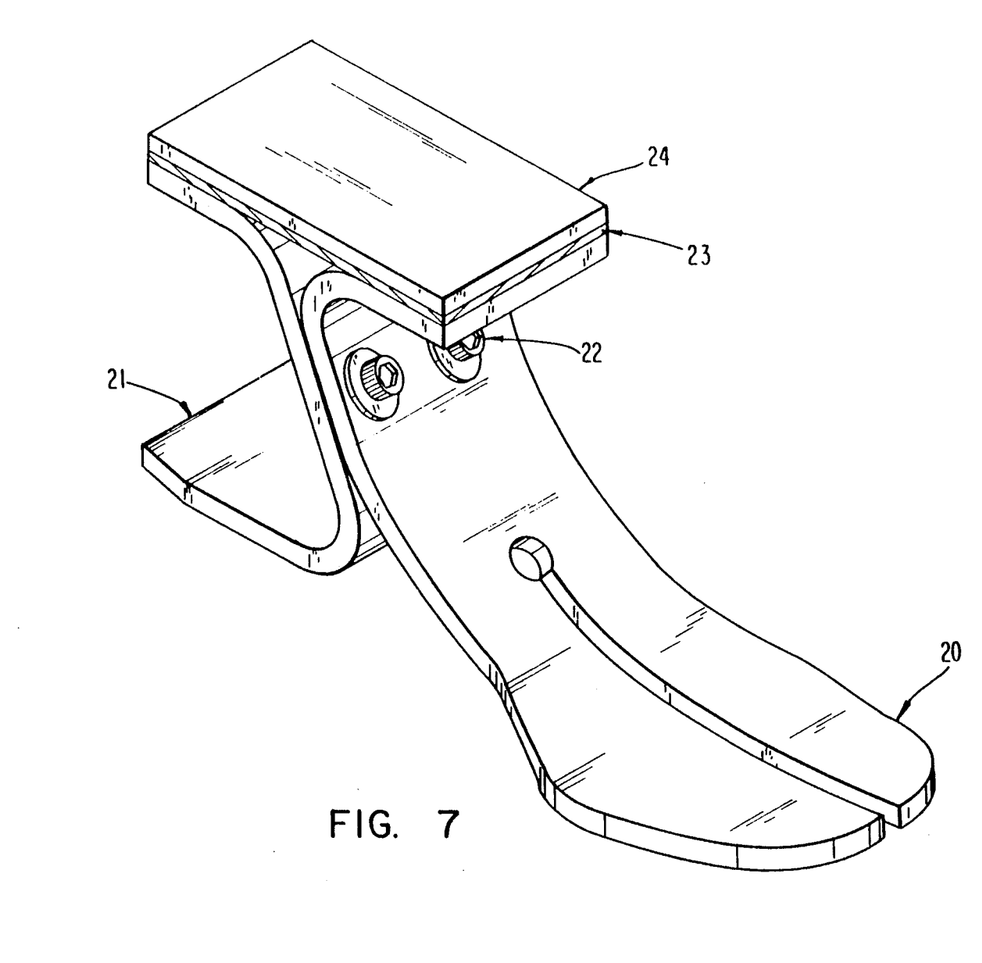
FIG. 7 is a 3-D view of the device of FIG. 5 modified with a slit to provide for inversion/eversion.

FIG. 5 to FIG. 7 present a modified version of the design shown in FIG. 1 to FIG. 4. The foot consists of a forefoot portion 20 which extends horizontally backward from the front part of the ankle region and curves downward and forward towards the toe region at the front end thereof and a heel portion 21 which extends horizontally forward from the back part of ankle opposite to the horizontal ankle region of the forefoot portion and curves downward and extends backward to the posterior of the foot. Both the forefoot portion 20 and heel portion 21 are fastened together by bolts 22. An elastomeric ankle pad 23 is added for the purpose of increasing the compliance of the foot. The elastomeric ankle pad 23 is sandwiched between a rectangular plate 24 and the horizontal ankle regions. The foot is fabricated from a resin impregnated carbon woven fabric.

A major advantage of the designs disclosed is that both the forefoot portion and the heel portion are detachable. It provides flexibility in manufacturing and interchangeability of parts to match the individual needs of amputees.

Figure 8:
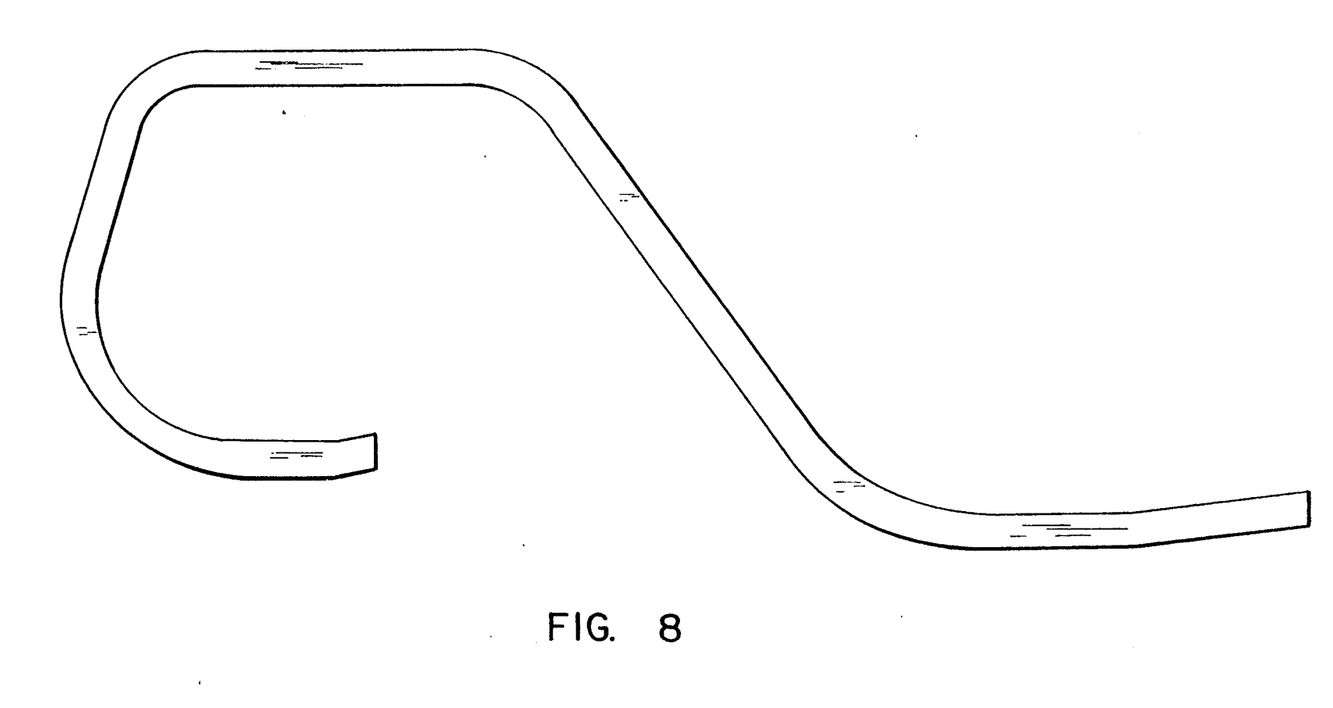
FIG. 8 is a side view of one invention.
Figure 9:
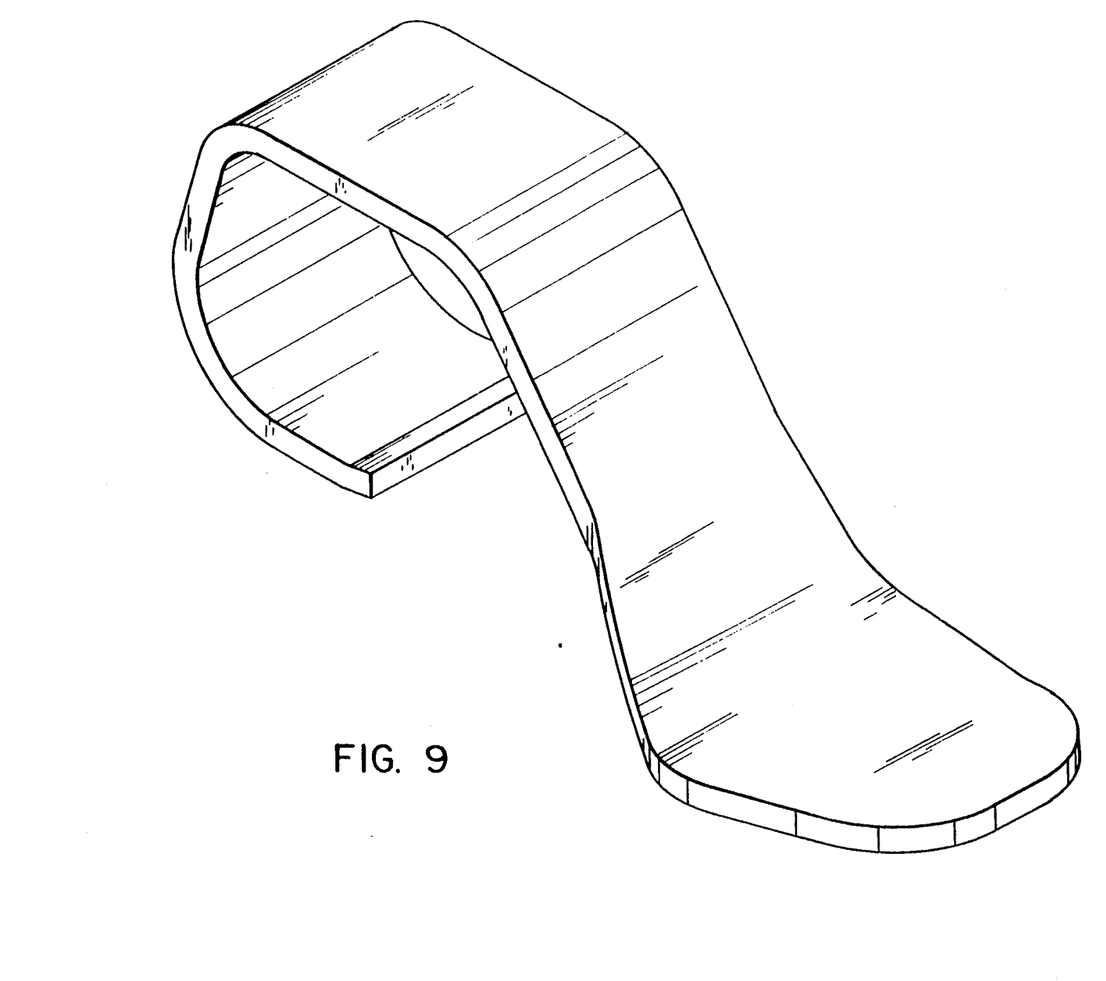
FIG. 9 is a 3-D view of the device of FIG. 8.
Figure 10:
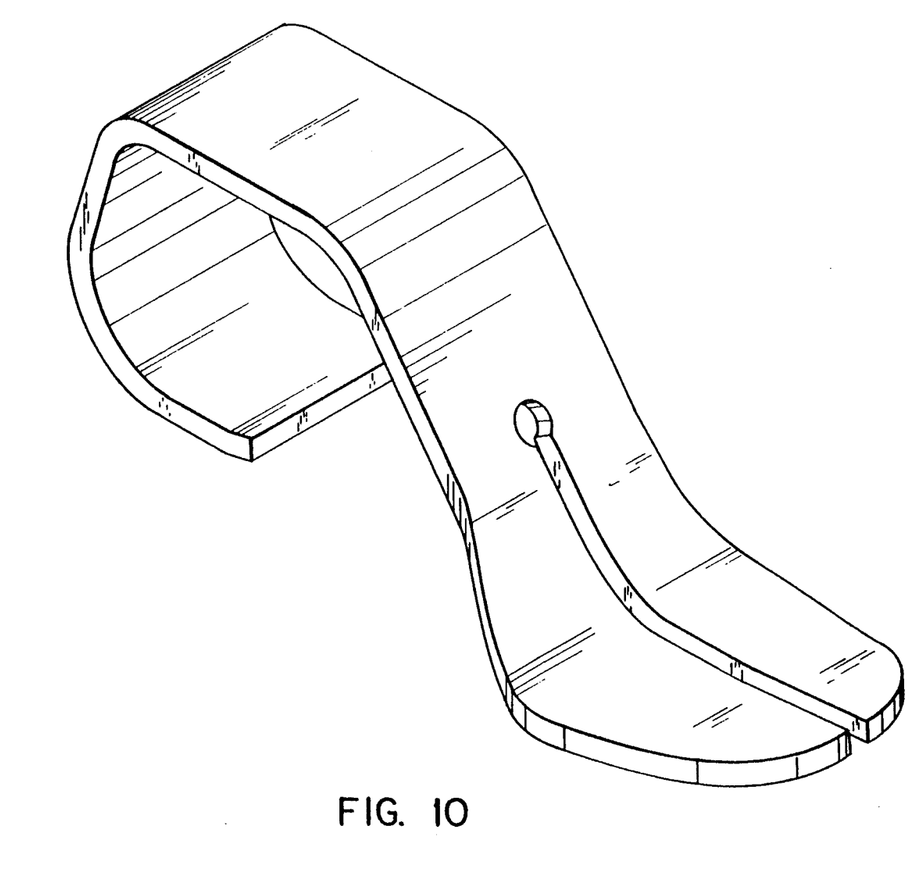
FIG. 10 is a 3-D view of the device of FIG. 8 modified with a slit to provide for inversion/eversion.

FIG. 8 and FIG. 9 are further modifications to the aforementioned designs. The entire forefoot is now fabricated as a single piece, with the heel portion and foot portion serving as spring-like leaves to provide the energy storing effect. Prosthetic foot fabricated as a single piece has a disadvantage that it must be custom made to suit different amputees. The present invention overcomes such a disadvantage, and does not require the use of mechanical fasteners.

Therefore, disclosed herein above, are six designs of composite prosthetic feet which allow an amputee to participate in various kinds of activities previously thought to be impossible. The feet are light-weight, durable and flexible to store and then release energy during each taken step.

What are claimed are:

1. A prosthetic foot, comprising a forefoot portion and a heel portion both of which are made of resin impregnated carbon woven fabric composite material to provide rebound characteristics and have generally horizontally extending connecting regions in an ankle region of the foot and connected to each other through an elastomeric ankle pad mounted to improve conformance with the foot; said heel portion being retroflexed downward from the horizontal connecting region thereof and extending to the posterior of the foot.

2. The prosthetic foot of claim 1, wherein a slit extends from a toe region in the forefoot portion up to approximately midway of the forefoot portion, said slit terminating in a hole of larger diameter than the width of said slit, the hole being capable of reducing the stress concentration at the hole end of said slit.

3. A prosthetic foot, comprising a forefoot portion and a heel portion both of which are made of resin impregnated carbon woven fabric composite material to provide rebound characteristics and which respectively have generally horizontally extending connecting regions opposed to each other, an elastomeric ankle pad mounted on said connecting regions, said pad being sandwiched between said horizontal regions and a generally rectangular plate on said pad to thereby improve conformance with the foot; said forefoot portion being curved downward and forward from its horizontal region toward a toe region at the front end thereof while said heel portion is curved downward from its horizontal connecting region to extend backward to the posterior of the foot; said forefoot portion and heel portion being connected together by mechanical fasteners at a region of contact.

4. The prosthetic foot of claim 3, wherein a slit extends from the toe region of the forefoot portion up to approximately midway of the forefoot portion, said slit terminating in a hole of larger diameter than the width of said slit, the hole being capable of reducing the stress concentration at the hole end of said slit.

* * * * *